United States Patent
Bamba et al.

(10) Patent No.: US 7,589,833 B2
(45) Date of Patent: Sep. 15, 2009

(54) FOREIGN MATTER INSPECTION APPARATUS AND FOREIGN MATTER INSPECTION METHOD

(75) Inventors: Yoshio Bamba, Hitachinaka (JP);
Masayuki Ochi, Kamisato (JP);
Shigehisa Nozawa, Kamisato (JP)

(73) Assignee: Hitachi High-Technologies Corporation, Tokyo (JP)

( * ) Notice: Subject to any disclaimer, the term of this patent is extended or adjusted under 35 U.S.C. 154(b) by 12 days.

(21) Appl. No.: 11/907,436

(22) Filed: Oct. 12, 2007

(65) Prior Publication Data
US 2008/0088848 A1   Apr. 17, 2008

(30) Foreign Application Priority Data
Oct. 16, 2006   (JP) .............................. 2006-281699

(51) Int. Cl.
*G01N 21/00* (2006.01)
(52) U.S. Cl. .................................................. 356/237.2
(58) Field of Classification Search ............... 356/237.2
See application file for complete search history.

(56) References Cited

U.S. PATENT DOCUMENTS 7,286,218 B2 *  10/2007  Tiemeyer et al. ......... 356/237.2
2005/0213086 A1    9/2005  Hamamatsu et al.

FOREIGN PATENT DOCUMENTS

JP         2005-283190         10/2005

* cited by examiner

*Primary Examiner*—Roy Punnoose
(74) *Attorney, Agent, or Firm*—McDermott Will & Emery LLP

(57) ABSTRACT

A foreign-matter inspection apparatus is implemented which allows the stable detection sensitivity to be maintained. A laser beam emitted from a laser apparatus is applied to a beam irradiation sample via an irradiation unit and a mirror. Then, the laser beam is captured into a beam-capturing camera via an image-forming lens and a beam-direction switching mirror. Based on the captured beam image, an image computational processing unit judges inclination of the laser beam, then adjusting the irradiation unit thereby to correct the inclination of the laser beam. Also, the beam is captured into the beam-capturing camera in specified number-of-times while focus of the laser beam is being changed by an arbitrary amount by the irradiation unit. Based on the captured beam, the focus of the laser beam is corrected by adjusting the irradiation unit.

18 Claims, 10 Drawing Sheets

FOREIGN MATTER INSPECTION APPARATUS AND FOREIGN MATTER INSPECTION METHOD

CLAIM OF PRIORITY

This application claims the benefit of Japanese Patent Application No. JP 2006-281699, filed on Oct. 16, 2006, the disclosure of which is incorporated herein by reference.

BACKGROUND OF THE INVENTION

The present invention relates to a foreign-matter inspection apparatus for detecting a foreign matter, scratch, defect, dirt, and the like existing on the surface of a inspection target such as a semiconductor wafer.

As disclosed in JP-A-2005-283190, in an apparatus for detecting a foreign matter (including scratch, defect, dirt, and the like) existing on the surface of a inspection target, e.g., a semiconductor wafer, the foreign matter is detected as follows: The surface of the semiconductor wafer is irradiated with laser light. Next, reflected light or scattered light is detected from the surface of the semiconductor wafer, thereby detecting the foreign matter existing on the surface thereof.

The laser beam, with which the surface of the semiconductor wafer is irradiated, is of a transversely-long elliptic shape. Moreover, the beam is emitted and applied thereto in a manner of being parallel to a camera. By maintaining this parallel state, i.e., by executing the beam irradiation in the same state always, it becomes possible to stabilize foreign-matter detection sensitivity of the foreign-matter inspection apparatus.

As described above, in the foreign-matter inspection apparatus, the foreign-matter detection sensitivity is stabilized by irradiating the surface of a inspection target with the laser light in the same state always.

In some cases, however, an assembly error occurs in the structure inside the foreign-matter inspection apparatus due to a reason such as time-lapse change. In this case, the beam with which the surface of the semiconductor wafer is irradiated cannot maintain the parallel state with respect to the camera. As a result, it turns out that the beam is emitted and applied to the semiconductor wafer in a state where the beam becomes oblique to the camera or the beam is not focused. When the beam cannot maintain the parallel state or the like with respect to the camera, the foreign-matter detection accuracy is dropped, and thus the sensitivity becomes lowered.

In the conventional technology, no consideration has been given to this point. Accordingly, there has existed a possibility that the foreign-matter detection sensitivity becomes unstable.

SUMMARY OF THE INVENTION

It is an object of the present invention to provide a foreign-matter inspection apparatus and foreign-matter inspection method which allows the stable detection sensitivity to be maintained.

There is provided a foreign-matter inspection method of the present invention for detecting a foreign matter by irradiating surface of a flat-plane-shaped inspection target with an ellipse-shaped laser beam, the foreign matter including scratch, defect, and dirt, and existing on the surface of the inspection target, the foreign-matter inspection method including the steps of irradiating the surface of a flat-plane portion of the beam irradiation sample with the generated laser beam, the beam irradiation sample being fixed to an inspection stage for the inspection target, photographing the laser beam by using a photographing unit, the laser beam being reflected from the beam irradiation sample, forming a beam image based on the laser beam photographed, calculating, from the beam image, an inclination angle of the laser beam's major axis or minor axis relative to a constant reference line, and correcting the inclination angle of the laser beam.

There is also provided a foreign-matter inspection method of the present invention, the foreign-matter inspection method including the steps of irradiating a flat-plane portion of a beam irradiation sample with a generated laser beam while changing focus width of a laser-beam-width focus adjustment unit and via the laser-beam-width focus adjustment unit, the beam irradiation sample being fixed to an inspection stage, forming a beam image based on the laser beam reflected from the beam irradiation sample, calculating, from the beam image, the width of the laser beam with which the flat-plane portion is irradiated, and setting, based on the width, the focus width of the laser-beam-width focus adjustment unit at a focus width in a case where the width of the laser beam with which the flat-plane portion is to be irradiated is the narrowest width.

There is provided a foreign-matter inspection apparatus of the present invention for detecting a foreign matter by irradiating surface of a flat-plane-shaped inspection target with an ellipse-shaped laser beam, the foreign matter including scratch, defect, and dirt, and existing on the surface of the inspection target, the foreign-matter inspection apparatus including a laser-beam generation unit, an inclination-angle adjustment unit for adjusting an inclination angle of the laser beam's major axis or minor axis relative to a constant reference line, a flat-plane portion irradiated with the laser beam via the inclination-angle adjustment unit, the beam irradiation sample fixed to an inspection stage, a photographing unit for photographing the laser beam reflected from the beam irradiation sample, an image formation unit for forming an image of the laser beam photographed, and a computational control unit for calculating, from the laser-beam image, the inclination angle of the laser beam's major axis or minor axis relative to the constant reference line, and correcting the inclination angle of the laser beam relative to the constant reference line by activating the inclination-angle adjustment unit.

There is also provided a foreign-matter inspection apparatus including a laser-beam-width focus adjustment unit for adjusting width of a laser beam generated from a laser-beam generation unit, a flat-plane portion irradiated with the laser beam via the laser-beam-width focus adjustment unit, a beam irradiation sample fixed to an inspection stage, a photographing unit for photographing the laser beam reflected from the beam irradiation sample, an image formation unit for forming a beam image based on the laser beam photographed, and a computational control unit for causing the laser beam to be generated from the laser-beam generation unit, irradiating the flat-plane portion of the beam irradiation sample with the generated laser beam while changing focus width of the laser-beam-width focus adjustment unit and via the laser-beam-width focus adjustment unit, calculating, from the beam image, the width of the laser beam with which the flat-plane portion is irradiated, the beam image being formed based on the laser beam photographed by the photographing unit, and setting, based on the calculated width of the laser beam, the focus width of the laser-beam-width focus adjustment unit at a focus width in a case where the width of the laser beam with which the flat-plane portion is to be irradiated is the narrowest width.

According to the present invention, a foreign-matter inspection apparatus and foreign-matter inspection method which allows the stable detection sensitivity to be maintained.

Other objects, features and advantages of the invention will become apparent from the following description of the embodiments of the invention taken in conjunction with the accompanying drawings.

DESCRIPTION OF THE INVENTION

Hereinafter, referring to the accompanying drawings, the explanation will be given below concerning embodiments of the present invention.

Figure 1:
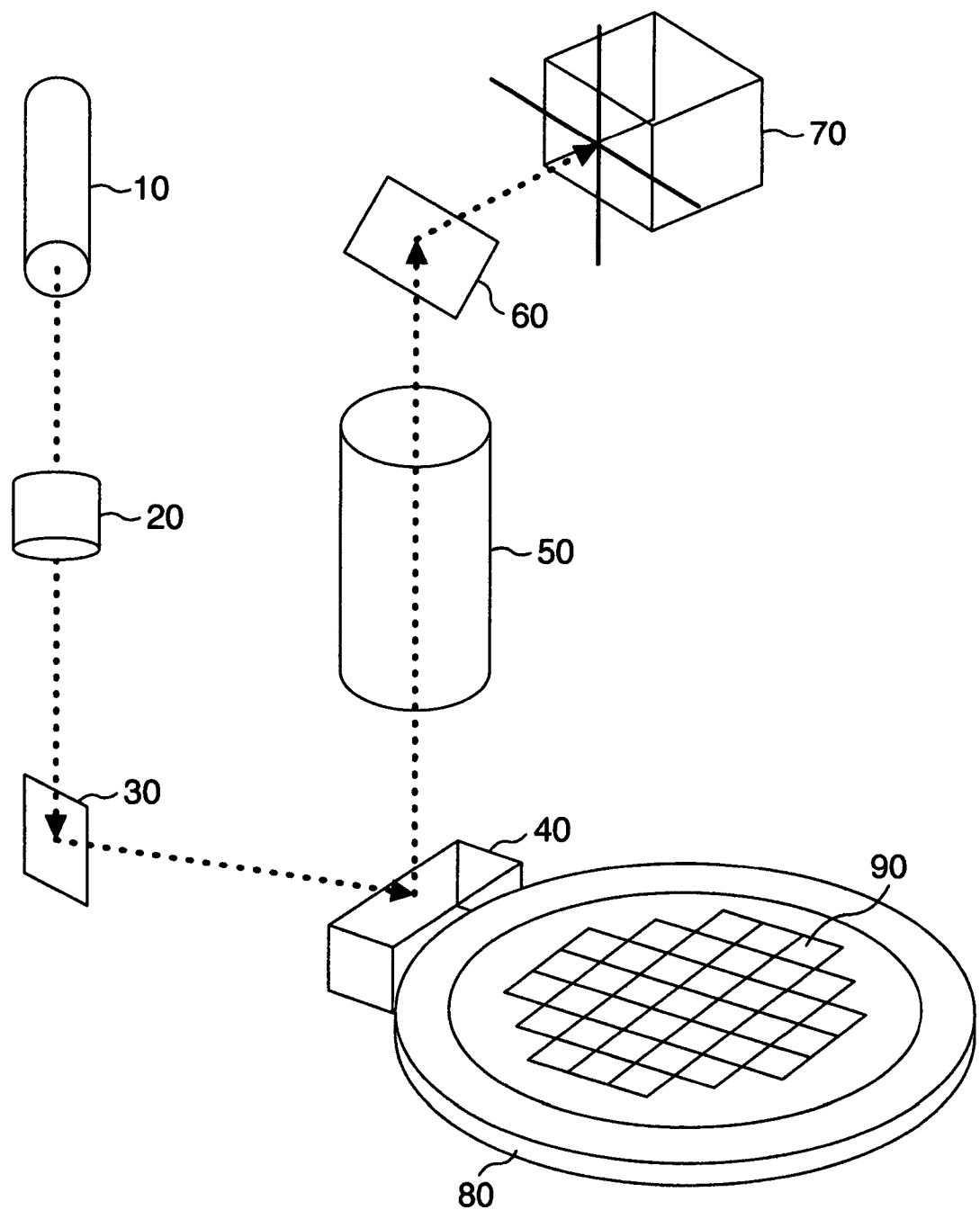
FIG. 1 is a schematic configuration diagram of a foreign-matter inspection apparatus which is an embodiment of the present invention.

FIG. 1 is a schematic configuration diagram of a foreign-matter inspection apparatus which is an embodiment of the present invention. This is the diagram where the present invention is applied to the foreign-matter inspection apparatus for inspecting a foreign matter existing on the surface of a semiconductor wafer. Incidentally, excluding components such as cover for covering the foreign-matter inspection apparatus, base, and operating table, FIG. 1 illustrates the schematic configuration extending from a laser apparatus to a stage of capturing a beam image. Additionally, a foreign matter, scratch, defect, dirt, and the like are generically referred to and defined as "foreign matter".

In FIG. 1, the foreign-matter inspection apparatus includes the laser apparatus 10, an irradiation unit 20, a beam-irradiation-angle switching mirror 30, a beam irradiation sample 40, an image-forming lens 50, a beam-direction switching mirror 60, a beam-capturing camera 70, and a flat-plane-shaped inspection stage 80. A semiconductor wafer 90, i.e., a flat-plane-shaped inspection target, is disposed on the inspection stage 80. A foreign matter or the like existing on the surface of this semiconductor wafer 90 is detected.

Here, the beam irradiation sample 40 is fixed to the inspection stage 80.

A foreign-matter inspection operation is performed as follows: The inspection stage 80 is scanned in the X and Y directions while irradiating the semiconductor wafer 90 on the inspection stage 80 with a light beam emitted from the laser apparatus 10. Then, the light beam emitted from the laser apparatus 10 passes through the irradiation unit 20. Moreover, the light beam is changed in its angle by the beam-irradiation-angle switching mirror 30, thereby being applied from an oblique direction to the semiconductor wafer 90 disposed on the inspection stage 80.

A scattered light of the light beam applied to the semiconductor wafer 90 is captured into the beam-capturing camera 70 via the image-forming lens 50 and the beam-direction switching mirror 60, thereby being recognized as a foreign matter.

An automatic adjustment operation of the foreign-matter detection sensitivity is automatically carried out immediately before carrying out the above-described foreign-matter inspection operation. Hereinafter, the explanation will be given below concerning the automatic adjustment operation of the foreign-matter detection sensitivity.

Figure 2:
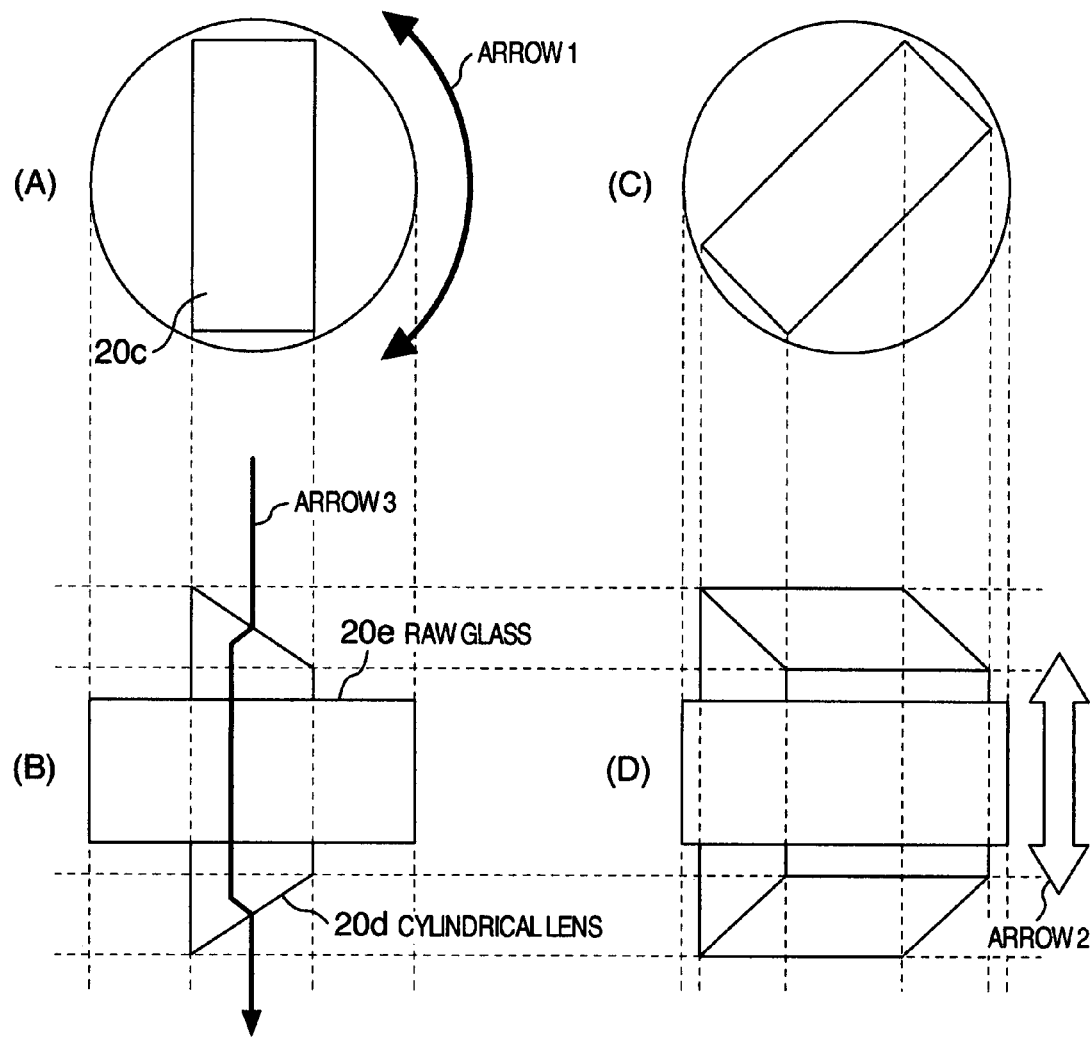
FIG. 2 is a diagram for illustrating an optical portion of the irradiation unit illustrated in FIG. 1.

FIG. 2 is a diagram for illustrating an optical portion of the irradiation unit 20. The diagram (A) in FIG. 2 illustrates a flat plane thereof, (B) illustrates a side plane thereof, (C) illustrates a flat plane of a state where the optical portion is rotated from the state in (A), and (D) illustrates a side plane of the state in (C). The optical portion includes two cylindrical lenses 20c and 20d and one raw glass 20e. The cylindrical lenses 20c and 20d are combined with each other in a folding-fan shapes with the raw glass 20e positioned therebetween.

The optical portion is not only rotatable as is indicated by an arrow 1, but also is movable in the up-and-down direction as is indicated by an arrow 2. The light beam emitted from the laser apparatus 10 passes through the optical portion as is indicated by an arrow 3. On account of this, rotating the optical portion as is indicated by the arrow 1 makes it possible to correct the inclination of the laser beam (i.e., inclination of the ellipse-shaped beam's major axis or minor axis relative to a constant reference line). Also, moving the optical portion in the up-and-down direction as is indicated by the arrow 2 makes it possible to focus width of the laser beam. Here, the constant reference line can be defined as a constant reference line on an image plane photographed by the beam-capturing camera 70.

Figure 3:
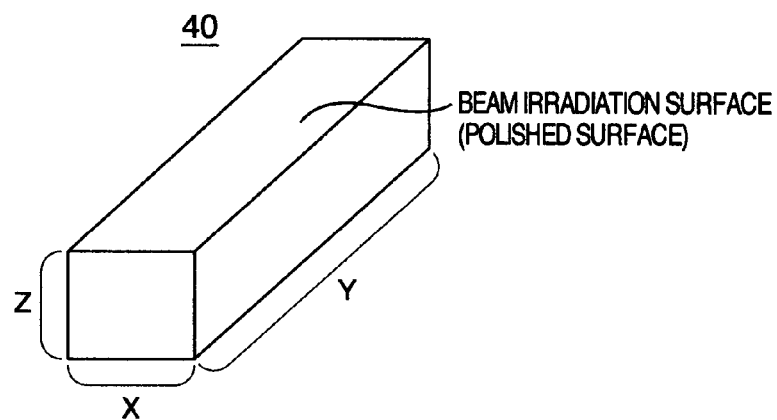
FIG. 3 is an explanatory diagram for explaining the beam irradiation sample illustrated in FIG. 1.

FIG. 3 is an explanatory diagram for explaining the beam irradiation sample 40. In FIG. 3, the raw material of which the beam irradiation sample 40 is composed is alumina ceramic (aluminum-oxide ceramic), which is low-cost, and is superior in abrasion-resistant property, heat-resistant property, and impact-resistant property. Moreover, beam irradiation surface of the beam irradiation sample 40 is polished so that the surface diffusely reflects the laser beam.

The beam irradiation sample 40 is mounted to the inspection stage 80. The dimension of the beam irradiation sample 40 is, e.g., about 40 mm in transverse dimension Y, about 10 mm in longitudinal dimension X, and about 10 mm in height dimension Z.

Figure 4:
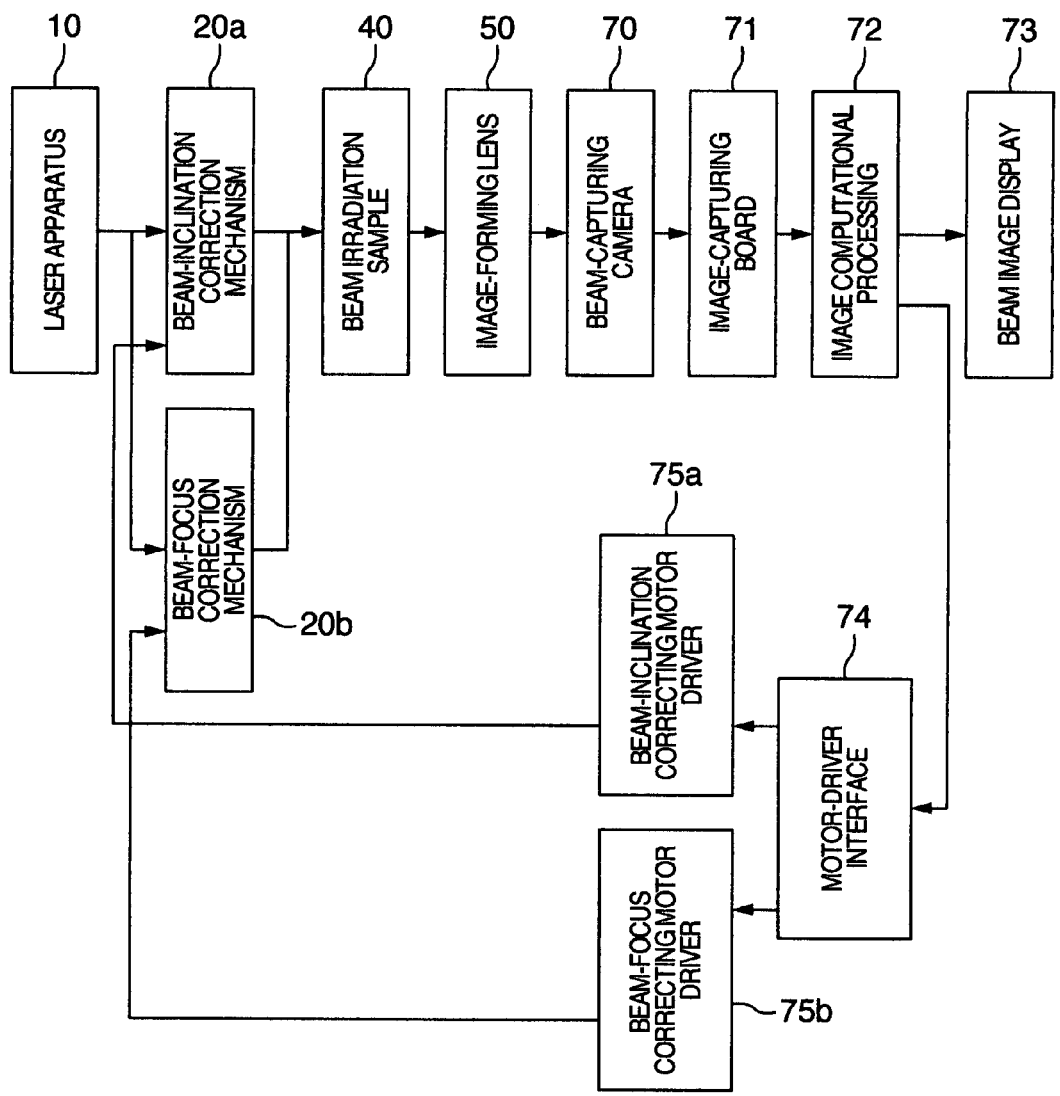
FIG. 4 is an operation-control functional block diagram of inclination correction and focus correction for the laser beam.

FIG. 4 is an operation-control functional block diagram of inclination correction and focus correction for the laser beam. Incidentally, in this operation-control functional block diagram, the mirrors 30 and 60 and the inspection stage 80 illustrated in FIG. 1 are omitted.

In FIG. 4, the laser beam emitted from the laser apparatus 10 passes through the irradiation unit 20, then being applied to the beam irradiation sample 40. Moreover, the beam applied to the beam irradiation sample 40 is reflected by this beam irradiation sample 40, thereby being captured into the beam-capturing camera 70 via the image-forming lens 50.

The beam image captured by the beam-capturing camera 70 is converted into an image file by an image-capturing board 71. Next, an image computational processing unit (i.e., computational control unit) 72 computes inclination correction amount and focus correction amount for the laser beam. The inclination correction amount and focus correction amount computed by the image computational processing unit 72 are respectively supplied to a beam-inclination correcting motor driver 75a and a beam-focus correcting motor driver 75b via a motor-driver interface 74.

The beam-inclination correcting motor driver 75a activates a beam-inclination correction mechanism 20a, thereby rotating the optical portion illustrated in FIG. 2, and correcting the inclination of the laser beam as was described above. Also, the beam-focus correcting motor driver 75b activates a beam-focus correction mechanism 20b, thereby moving the optical portion illustrated in FIG. 2 in the up-and-down direction, and correcting the focus of the laser beam as was described above.

The laser beam whose inclination and focus have been corrected passes through the same route as the above-described one, then being supplied into the image-capturing board 71. Moreover, the laser beam is converted into the image file, then being image-displayed on a display 73 by the image computational processing unit 72.

Incidentally, the image computational processing unit 72 is configured with a computer. In accordance with computer programs, the unit 72 performs the laser-beam inclination correction and width correction of the irradiation unit 20. Also, the unit 72 performs operation controls over the mirrors 30 and 60 and the inspection stage 80.

Figure 5:
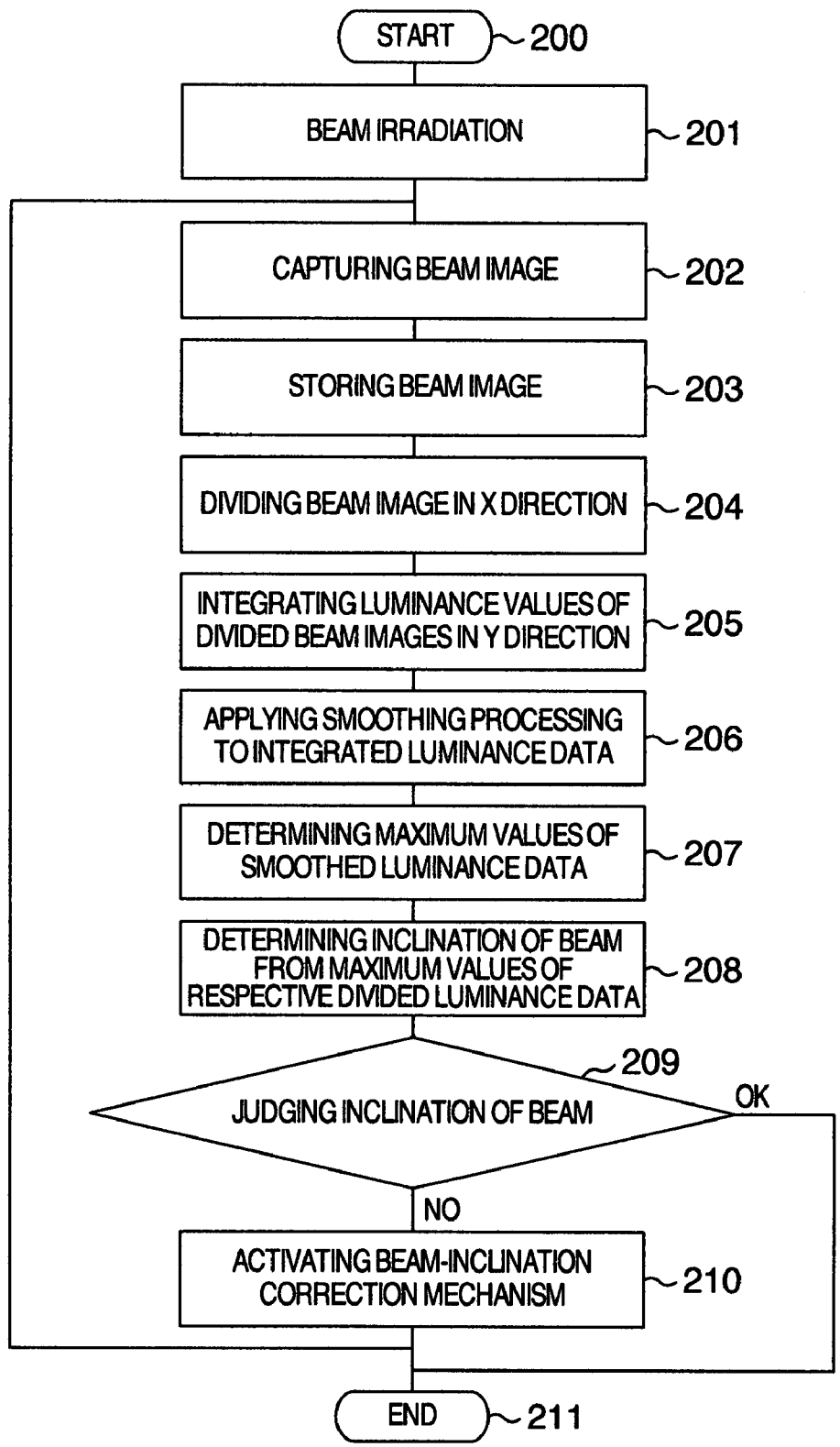
FIG. 5 is an inclination-correction operation flowchart of the laser beam in the embodiment of the present invention.

FIG. 5 is a flowchart (which is also available for flowchart for computer program) ranging from the beam irradiation to adjusting and setting the beam inclination at an optimum value.

In FIG. 5, at the time of the detection-sensitivity automatic adjustment, the laser beam emitted from the laser apparatus 10 passes through the above-described route, then being applied to the beam irradiation sample 40. Next, the light beam is captured into the beam-capturing camera 70 via the image-forming lens 50 and the beam-direction switching mirror 60 (steps 201 and 202). Moreover, the captured beam image is stored into the file, and then the stored image file is divided in the X direction and is read by the image computational processing unit 72 (steps 203 and 204). The divided and read data, which are luminance data, are quantified into numerical values. Furthermore, the image computational processing unit 72 integrates the quantified data in the Y direction (step 205).

In addition, the image computational processing unit 72 applies a smoothing processing to the integrated data in order to eliminate noise components from the integrated data (step 206). Then, the unit 72 acquires Y coordinates each of which corresponds to a maximum value of the numerical values of the divided and smoothed data (step 207). Finally, the unit 72 plots, into a graph, the Y coordinates each of which corresponds to the maximum value, then determining the inclination from this graph (step 208).

Figure 6A:
FIG. 6A is a diagram for illustrating the inclination of the laser beam in the embodiment of the present invention.
Figure 6B:
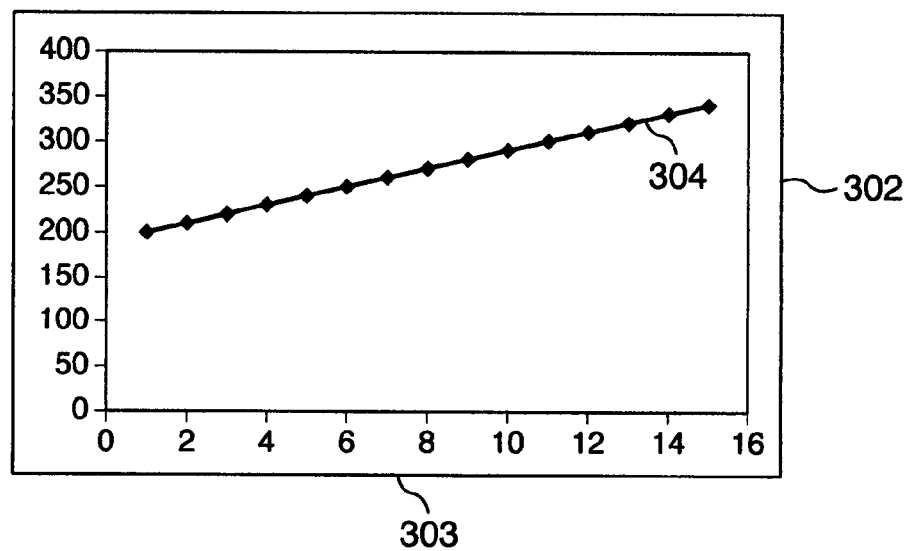
FIG. 6B is a diagram for illustrating the inclination of the laser beam in the embodiment of the present invention, using a numerical value diagram.

FIG. 6A is a diagram for illustrating the beam image in the case where the transversely-long-ellipse-shaped laser beam is inclined. FIG. 6B is a diagram for illustrating the data on the Y coordinates of the maximum values of the divided and smoothed luminance values. In FIG. 6A, a reference numeral 301 denotes the beam irradiation portion, and 300 denotes a portion which is not irradiated with the beam. Also, 302 denotes the Y axis (longitudinal axis) of the beam image, 303 denotes the X axis (transverse axis) of the beam image, and 304 denotes the Y coordinates of the maximum values at the time when the luminance values within the width divided in the X direction are integrated in the Y direction. A linear straight-line expression $y=ax+b$ is determined from the graph illustrated in FIG. 6B, thereby calculating the inclination a (step 208).

At this time, if the inclination a falls within an apparatus-sensitivity tolerance range, no correction operation is executed, then terminating the operation flow (steps 209 and 211).

Meanwhile, if, at the step 209, the inclination a falls outside the apparatus-sensitivity tolerance range, the beam-inclination correction mechanism 20a is activated, then getting back to the step 202 (steps 209 and 210).

Figure 7A:
FIG. 7A is a diagram for illustrating a case where the inclination of the laser beam in the embodiment of the present invention is corrected.
Figure 7B:
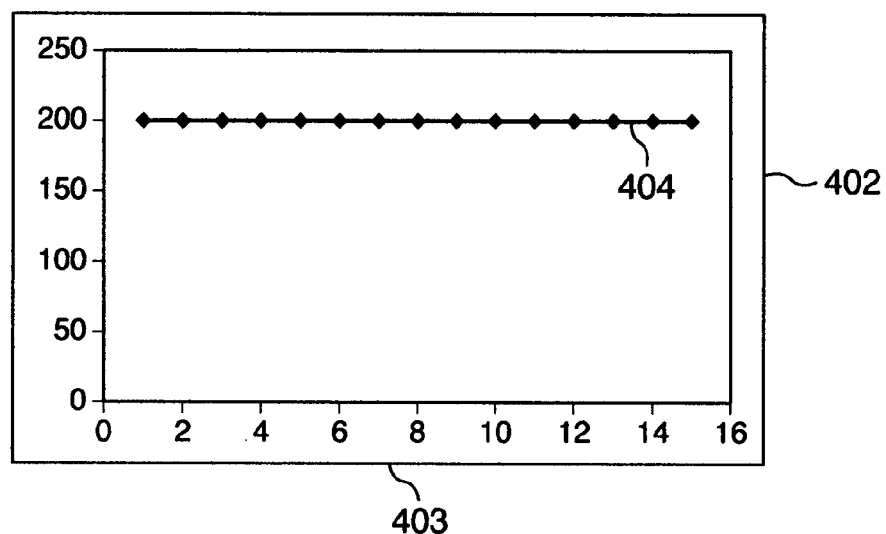
FIG. 7B is a diagram for illustrating the case where the inclination of the laser beam in the embodiment of the present invention is corrected, using a numerical value diagram.

FIG. 7A is a diagram for illustrating the beam after the beam inclination has been adjusted. FIG. 7B is a diagram for illustrating a graph of the maximum data on the luminance values after the beam inclination has been adjusted. In FIG. 7A, a reference numeral 401 denotes the beam irradiation portion, and 400 denotes a portion which is not irradiated with the beam. Also, 402 denotes the Y axis of the beam image, 403 denotes the X axis of the beam image, and 404 denotes the Y coordinates of the maximum values at the time when the luminance values within the width divided in the X direction are integrated in the Y direction.

As illustrated in FIG. 7A and FIG. 7B, it can be judged that the beam inclination has been corrected. FIG. 6A and FIG. 7A may be displayed on the display 73 at the time of the detection-sensitivity adjustment. Otherwise, FIG. 6A and FIG. 7A may be displayed on the display 73 at the time of the maintenance alone for confirming the beam inclination.

Next, the explanation will be given below concerning the focus correction for the laser beam. In this beam focus correction, the focus of the beam is automatically recognized, and is adjusted at a position at which the beam is focused most. The position at which the beam is focused most is a position at which the width of the beam is the narrowest.

Figure 8:
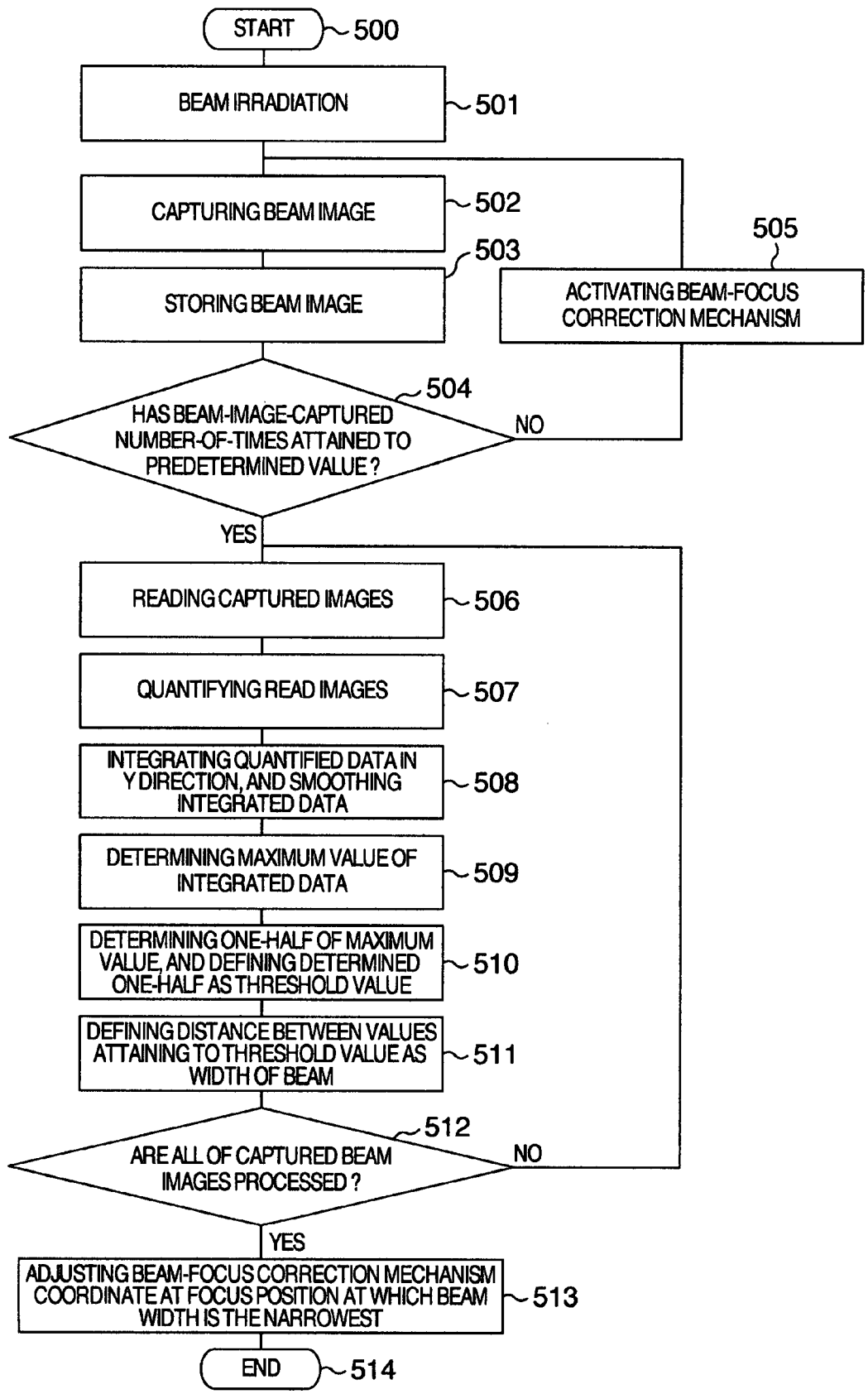
FIG. 8 is a focus-correction operation flowchart of the laser beam in the embodiment of the present invention.

FIG. 8 is an operation flowchart for adjusting and setting the focus position of the laser beam at an optimum value, i.e., the focus-correction operation flowchart (which is also available for flowchart for computer program).

Steps 501 to 503 in FIG. 8 are basically the same operations as the ones at the steps 201 to 203 in FIG. 5. At a step 504, it is judged whether or not the beam-image-captured number-of-times has attained to a predetermined value. If the beam-image-captured number-of-times has not attained to the predetermined value, the processing proceeds to a step 505. At this step 505, the beam-focus correction mechanism 20b is activated by an arbitrary displacement amount, then getting back to the step 502.

Meanwhile, if, at the step 504, the beam-image-captured number-of-times has attained to the predetermined value, the processing proceeds to a step 506, where the data are read from the stored image file. The read data, which are luminance data, are quantified into numerical values (step 507). Moreover, the quantified data are integrated in the Y direction, then being smoothed (step 508).

The maximum value of the integrated and smoothed data is determined (step 509). A value is determined which is equal to the one-half of the maximum value determined, then defining and employing this value as a threshold value (step 510). Furthermore, the distance between both ends of the luminance data attaining to the threshold value is defined as the width of the beam (step 511). The steps 506 to 511 are repeated until all of the captured beam images have been processed (step 512).

Figure 9:
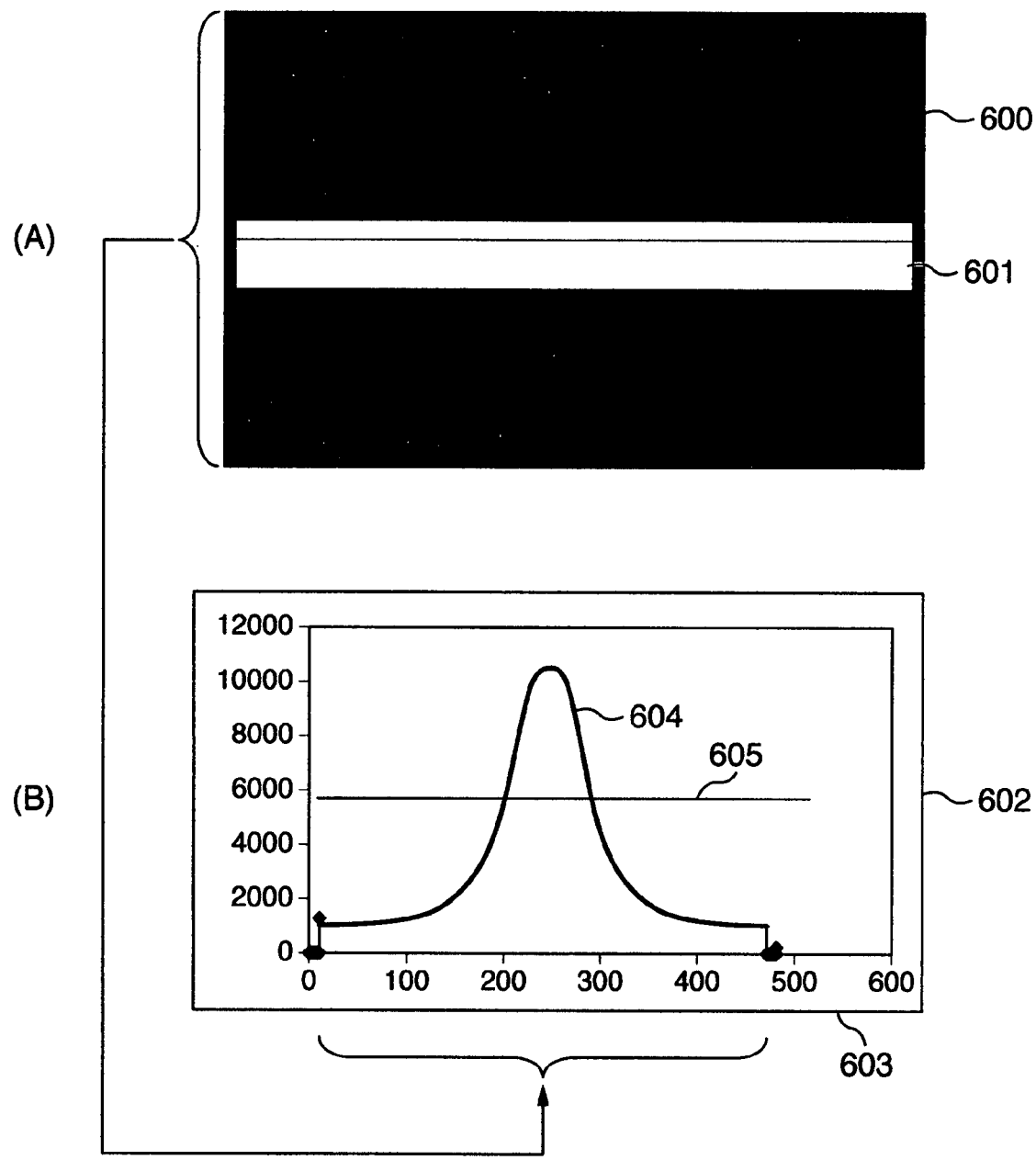
FIG. 9 is a diagram for illustrating width of the laser beam in the embodiment of the present invention, and a diagram for illustrating the width using a numerical value diagram.

A diagram (A) in FIG. 9 illustrates the beam width at the time of determining the width of the beam. A diagram (B) in FIG. 9 is a graph indicating numerical value data on the beam width. A reference numeral 601 denotes the beam irradiation portion, and 600 denotes a portion which is not irradiated with the beam. Also, 602 denotes the Y axis of the beam images, 603 denotes the X axis of the beam images, 604 denotes the luminance value resulting from integrating the beam images in the Y direction, and 605 denotes the one-half of the maximum luminance value.

From all of the captured beam images, a position of the beam-focus correction mechanism 20b at which the beam width is the narrowest is calculated. Then, the beam-focus correction mechanism 20b is adjusted and set at the beam-focus correction mechanism coordinate at which the beam width is the narrowest (steps 513 and 514).

Figure 10:
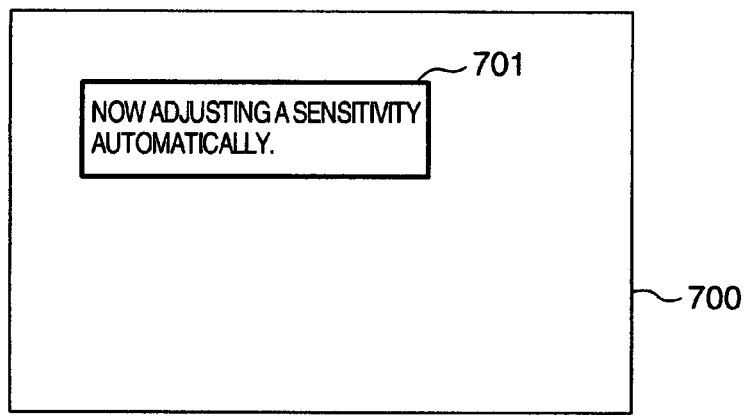
FIG. 10 is a diagram for illustrating a screen display example indicating that carry-out of the sensitivity automatic adjustment is underway in the embodiment of the present invention.
Figure 11:
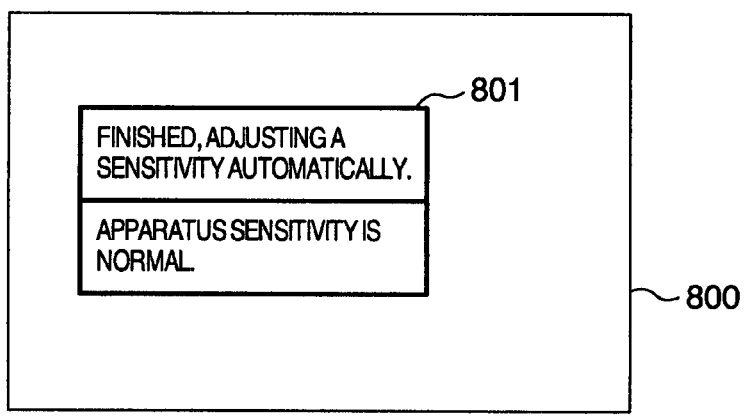
FIG. 11 is a diagram for illustrating a screen display example indicating termination of the sensitivity automatic adjustment in the embodiment of the present invention, and its result in the embodiment of the present invention.

FIG. 10 is a diagram for illustrating a screen 700 of a message character string 701 displayed on the display while carry-out of the sensitivity automatic adjustment is underway in the embodiment of the present invention. Also, FIG. 11 is a diagram for illustrating a screen 800 of a message character string 801 displayed on the display when the sensitivity automatic adjustment is over in the embodiment of the present invention.

As illustrated in FIG. 10, the message 701 of "Now Adjusting a sensitivity automatically" is displayed while execution of the sensitivity automatic adjustment is underway. As illustrated in FIG. 11, the message 801 of "Apparatus sensitivity is normal" is displayed when the sensitivity automatic adjustment is over normally. In FIG. 11, a message of "Apparatus sensitivity is abnormal" is displayed at the time of abnormality.

Figure 12:
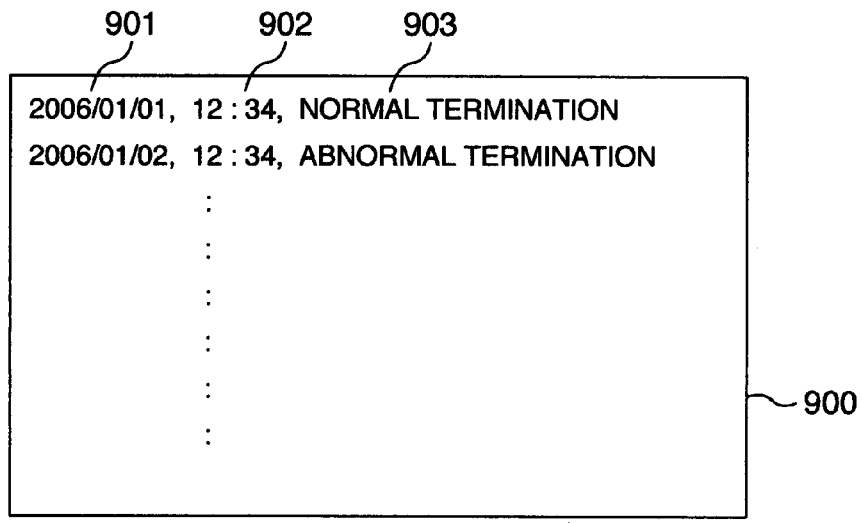
FIG. 12 is a diagram for illustrating an example of a result log file after the termination of the sensitivity automatic adjustment in the embodiment of the present invention.

FIG. 12 is a diagram for illustrating a log file for recording the history which remains when the sensitivity automatic adjustment is carried out in the embodiment of the present invention. Requirements to be recorded in FIG. 12 are date 901, time 902, and a message 903 indicating whether the termination when the sensitivity automatic adjustment is carried out is a normal termination or an abnormal termination.

In the above-described example, either of the laser-beam inclination correction and the laser-beam focus correction may be executed. Otherwise, both of them may be executed.

Figure 13:
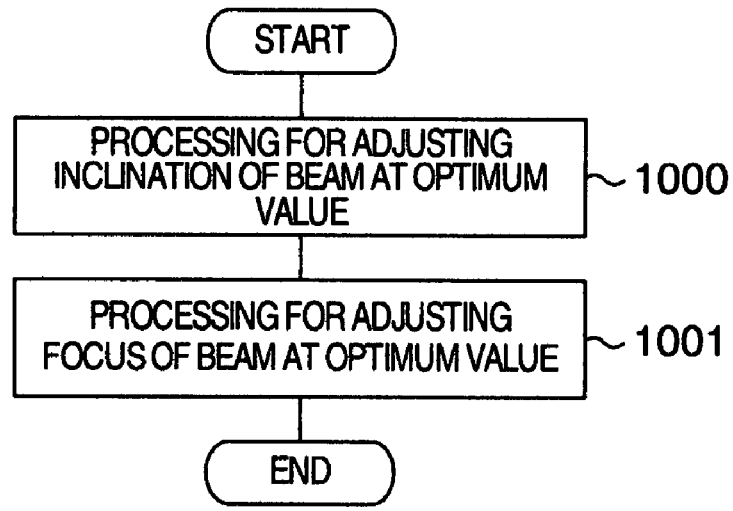
FIG. 13 is a diagram for illustrating an example of an operation flowchart in a case where the laser-beam inclination correction and the laser-beam focus correction are continuously executed.

FIG. 13 is a diagram for illustrating a flowchart in the case where both of the laser-beam inclination correction and the laser-beam focus correction are executed. In FIG. 13, the laser-beam inclination correction illustrated in FIG. 5 is executed at a step 1000. After that, the laser-beam focus correction illustrated in FIG. 8 is executed at a step 1001.

Figure 14:
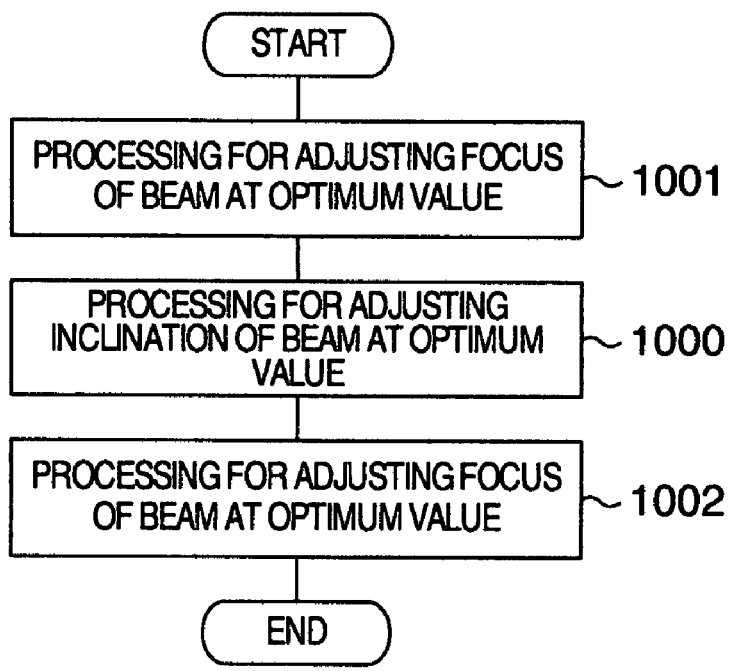
FIG. 14 is a diagram for illustrating another example of the operation flowchart in the case where the laser-beam inclination correction and the laser-beam focus correction are continuously executed.

When both of the laser-beam inclination correction and the laser-beam focus correction are executed, as illustrated in FIG. 14, the laser-beam focus correction (step 1001) is executed, and the laser-beam inclination correction (step 1000) is executed. After that, the laser-beam focus correction (step 1002) may be executed once again in order to implement an enhancement in the accuracy.

As having been explained so far, according to the present invention, it becomes possible to implement the foreign-matter inspection apparatus, foreign-matter inspection method, and computer program for the foreign-matter inspection apparatus which allows the stable detection sensitivity to be maintained.

Namely, even if an imposition error occurs in the structure inside the foreign-matter inspection apparatus due to a reason such as time-lapse change, the inclination and focus of the laser beam can be automatically adjusted and set into a constant state before the foreign-matter inspection operation. This feature makes it possible to prevent a lowering in the foreign-matter detection sensitivity, thereby allowing the stable detection sensitivity to be maintained.

Incidentally, the above-described embodiment is an embodiment in the case where the present invention is applied to the foreign-matter inspection apparatus for detecting a foreign matter existing on a semiconductor-wafer surface. Not being limited to the semiconductor wafer, however, the present invention is also applicable to surface foreign-matter inspections in the other flat-plane-shaped inspection targets.

It should be further understood by those skilled in the art that although the foregoing description has been made on embodiments of the invention, the invention is not limited thereto and various changes and modifications may be made without departing from the spirit of the invention and the scope of the appended claims.

The invention claimed is:

1. A foreign-matter inspection method for detecting a foreign matter on a inspection target, comprising:
    a laser-beam generation step of generating a laser beam with which said inspection target is to be irradiated,
    a measurement step of measuring characteristics of said laser beam generated at said laser-beam generation step,
    a modification step of modifying said characteristics of said laser beam based on a measurement result of said measurement step,
    a detection step of irradiating said inspection target with said laser beam, and detecting a reflected light or scattered light from said inspection target, and
    a processing step of detecting said foreign matter on said inspection target based on an output obtained at said detection step.

2. The foreign-matter inspection method according to claim 1, wherein said laser-beam generation step is a laser-beam generation step for irradiating a flat-plane-shaped inspection target with an ellipse-shaped laser beam,
    said measurement step, further comprising:
    a step of irradiating a flat-plane portion of a beam irradiation sample with said laser beam, said beam irradiation sample being fixed to an inspection stage on which said inspection target is located,
    a step of photographing said laser beam by using a photographing unit, said laser beam being reflected from said flat-plane portion of said beam irradiation sample, and
    a step of forming a beam image based on said laser beam photographed, said modification step, further comprising:
a step of calculating, from said beam image, inclination angle of said laser beam's major axis or minor axis relative to a constant reference line, and
a step of correcting said inclination angle of said laser beam.

3. The foreign-matter inspection method according to claim 2, wherein
said correction for said inclination angle of said laser beam is performed for each timing before said surface foreign-matter inspection on said inspection target.

4. The foreign-matter inspection method according to claim 2, further comprising the steps of:
quantifying, as luminance data, said formed beam image into numerical values,
dividing said quantified data in a transverse-axis direction of said beam image,
integrating said divided numerical-value data in a longitudinal-axis direction of said beam image,
smoothing said integrated numerical-value data, and determining maximum values thereof,
calculating a linear straight line in accordance with said respective maximum values determined, and
calculating said inclination angle of said laser beam from an inclination of said calculated linear straight line.

5. The foreign-matter inspection method according to claim 1, wherein
said laser-beam generation step is a laser-beam generation step for irradiating a flat-plane-shaped inspection target with an ellipse-shaped laser beam,
said measurement step, further comprising:
a step of irradiating a flat-plane portion of a beam irradiation sample with said generated laser beam while changing focus width of a laser-beam-width focus adjustment unit and via said laser-beam-width focus adjustment unit, said beam irradiation sample being fixed to an inspection stage on which said inspection target is located, and
a step of forming a beam image based on said laser beam reflected from said flat-plane portion of said beam irradiation sample,
said modification step, further comprising:
a step of calculating, from said beam image, width of said laser beam with which said flat-plane portion is irradiated, and
a step of setting, based on said calculated width of said laser beam, said focus width of said laser-beam-width focus adjustment unit at a focus width in a case where said width of said laser beam with which said flat-plane portion is to be irradiated is the narrowest width.

6. The foreign-matter inspection method according to claim 5, wherein
said setting to said focus width in said case where said width of said laser beam is said narrowest width is performed for each timing before said surface foreign-matter inspection on said inspection target.

7. The foreign-matter inspection method according to claim 5, further comprising the steps of:
quantifying, as luminance data, said formed beam image into numerical values,
integrating said quantified data in a longitudinal-axis direction of said beam image,
smoothing said integrated numerical-value data, and determining a maximum value thereof,
defining a value as a threshold value, said value being equal to one-constant-numberth of said maximum value, and
calculating, as said width of said laser beam, distance between said numerical-value data corresponding to said threshold value.

8. The foreign-matter inspection method according to claim 1, wherein
said laser-beam generation step is a laser-beam generation step for irradiating a flat-plane-shaped inspection target with an ellipse-shaped laser beam,
said measurement step, further comprising:
a step of irradiating a flat-plane portion of a beam irradiation sample with said generated laser beam, said beam irradiation sample being fixed to an inspection stage on which said inspection target is located,
a step of photographing said laser beam by using a photographing unit, said laser beam being reflected from said flat-plane portion of said beam irradiation sample,
a step of forming a beam image based on said laser beam photographed,
a step of irradiating said flat-plane portion of said beam irradiation sample with said generated laser beam while changing focus width of a laser-beam-width focus adjustment unit and via said laser-beam-width focus adjustment unit,
a step of forming a beam image based on said laser beam reflected from said flat-plane portion of said beam irradiation sample, and
a step of calculating, from said beam image, width of said laser beam with which said flat-plane portion is irradiated,
said modification step, further comprising:
a step of calculating, from said beam image, inclination angle of said laser beam's major axis or minor axis relative to a constant reference line, and a step of correcting said inclination angle of said laser beam, and
a step of setting, based on said calculated width of said laser beam, said focus width of said laser-beam-width focus adjustment unit at a focus width in a case where said width of said laser beam with which said flat-plane portion is to be irradiated is the narrowest width.

9. The foreign-matter inspection method according to claim 8, wherein
said correction for said inclination angle of said laser beam and said setting to said focus width in said case where said width of said laser beam is said narrowest width are performed for each timing before said surface foreign-matter inspection on said inspection target.

10. A foreign-matter inspection apparatus for detecting a foreign matter on a inspection target, comprising:
a laser-beam generation unit for generating a laser beam with which said inspection target is to be irradiated,
a measurement unit for measuring characteristics of said laser beam generated from said laser-beam generation unit,
a modification unit for modifying said characteristics of said laser beam based on a measurement result of said measurement unit,
a detection unit for irradiating said inspection target with said laser beam, and detecting a reflected light or scattered light from said inspection target, and
a processing unit for detecting said foreign matter on said inspection target based on an output of said detection unit.

11. The foreign-matter inspection apparatus according to claim 10, wherein
said laser beam is of an elliptic shape,
said foreign matter including scratch, defect, and dirt which exist on a surface of said inspection target, said measurement unit, comprising:
an inclination-angle adjustment unit for adjusting inclination angle of said laser beam's major axis or minor axis relative to a constant reference line, said laser beam being generated from said laser-beam generation unit,
a flat-plane portion irradiated with said laser beam via said inclination-angle adjustment unit, said laser beam being generated from said laser-beam generation unit,
a beam irradiation sample fixed to an inspection stage on which said inspection target is located,
a photographing unit for photographing said laser beam reflected from said flat-plane portion of said beam irradiation sample, and
an image formation unit for forming an image of said laser beam photographed by said photographing unit,
said modification unit, comprising:
a computational control processing unit for
calculating, from said laser beam image, said inclination angle of said laser beam's major axis or minor axis relative to said constant reference line, and
activating said inclination-angle adjustment unit, and correcting said inclination angle of said laser beam relative to said constant reference line.

12. The foreign-matter inspection apparatus according to claim 11, wherein
said computational control processing unit
quantifies, as luminance data, said formed beam image into numerical values,
divides said quantified data in a transverse-axis direction of said beam image,
integrates said divided numerical-value data in a longitudinal-axis direction of said beam image,
smoothes said integrated numerical-value data, and determines maximum values thereof,
calculates a linear straight line in accordance with said respective maximum values determined, and
calculates said inclination angle of said laser beam from an inclination of said calculated linear straight line.

13. The foreign-matter inspection apparatus according to claim 12, further comprising:
an image display unit,
said computational control processing unit causing said image display unit to display said calculated linear straight line.

14. The foreign-matter inspection apparatus according to claim 10, wherein
said laser beam is of an elliptic shape,
said foreign matter including scratch, defect, and dirt which exist on a surface of said inspection target,
said measurement unit, comprising:
a laser-beam-width focus adjustment unit for adjusting width of said laser beam generated from said laser-beam generation unit,
a flat-plane portion irradiated with said laser beam via said laser-beam-width focus adjustment unit, said laser beam being generated from said laser-beam generation unit,
a beam irradiation sample fixed to an inspection stage on which said inspection target is located,
a photographing unit for photographing said laser beam reflected from said flat-plane portion of said beam irradiation sample, and
an image formation unit for forming an image of said laser beam based on said laser beam photographed by said photographing unit,
said measurement unit
causing said laser beam to be generated from said laser-beam generation unit,
irradiating said flat-plane portion of said beam irradiation sample with said generated laser beam while changing focus width of said laser-beam-width focus adjustment unit and via said laser-beam-width focus adjustment unit, said beam irradiation sample being fixed to said inspection stage on which said inspection target is located, and
photographing said laser beam by said photographing unit, said modification unit, comprising:
a computational control processing unit for
calculating, from said photographed beam image, said width of said laser beam with which said flat-plane portion is irradiated, and
setting, based on said calculated width of said laser beam, said focus width of said laser-beam-width focus adjustment unit at a focus width in a case where said width of said laser beam with which said flat-plane portion is to be irradiated is the narrowest width.

15. The foreign-matter inspection apparatus according to claim 14, wherein
said computational control processing unit
quantifies, as luminance data, said formed beam image into numerical values,
integrates said quantified data in a longitudinal-axis direction of said beam image,
smoothes said integrated numerical-value data, and determines a maximum value thereof,
defines a value as a threshold value, said value being equal to one-constant-numberth of said maximum value, and
calculates, as said width of said laser beam, distance between said numerical-value data corresponding to said threshold value.

16. The foreign-matter inspection apparatus according to claim 14, further comprising:
an image display unit,
said computational control processing unit causing said image display unit to display an image for indicating said calculated width of said laser beam.

17. The foreign-matter inspection apparatus according to claim 14, wherein
said laser beam is of an elliptic shape,
said foreign matter including scratch, defect, and dirt which exist on a surface of said inspection target,
said measurement unit, comprising:
a laser-beam irradiation unit for adjusting inclination angle of said laser beam's major axis or minor axis relative to a constant reference line, and said width of said laser beam, said laser beam being generated from said laser-beam generation unit,
a flat-plane portion irradiated with said laser beam via said laser-beam irradiation unit, said laser beam being generated from said laser-beam generation unit,
a beam irradiation sample fixed to an inspection stage on which said inspection target is located,
a photographing unit for photographing said laser beam reflected from said flat-plane portion of said beam irradiation sample, and
an image formation unit for forming an image of said laser beam based on said laser beam photographed by said photographing unit,
said modification unit, comprising:
a computational control processing unit for
calculating, from said laser beam image, said inclination angle of said laser beam's major axis or minor axis relative to said constant reference line,
activating said laser-beam irradiation unit, and correcting said inclination angle of said laser beam relative to said constant reference line, causing said laser beam to be generated from said laser-beam generation unit, irradiating said flat-plane portion of said beam irradiation sample with said generated laser beam while changing said width of said laser beam by said laser-beam irradiation unit and via said laser-beam irradiation unit, calculating, from said beam image, said width of said laser beam with which said flat-plane portion is irradiated, said beam image being formed based on said laser beam photographed by said photographing unit, and setting, based on said calculated width of said laser beam, said laser-beam focus width of said laser-beam irradiation unit at a focus width in a case where said width of said laser beam with which said flat-plane portion is to be irradiated is the narrowest width.

18. A beam irradiation sample used for a foreign-matter inspection apparatus for irradiating a surface of a flat-plane-shaped inspection target with a laser beam, and detecting a foreign matter, said foreign matter including scratch, defect, and dirt which exist on said surface of said inspection target, said foreign-matter inspection apparatus, comprising:

a laser-beam generation unit for generating an ellipse-shaped laser beam, a laser-beam adjustment unit for adjusting inclination or width of said laser beam generated from said laser-beam generation unit, said beam irradiation sample irradiated with said laser beam via said laser-beam adjustment unit, and fixed to an inspection stage on which said inspection target is located, said laser beam being generated from said laser-beam generation unit, a photographing unit for photographing said laser beam reflected from a flat-plane portion of said beam irradiation sample, an image formation unit for forming an image of said laser beam photographed by said photographing unit, and a computational control processing unit for correcting said inclination or width of said laser beam based on said image of said laser beam, wherein said beam irradiation sample is composed of a rectangle-shaped aluminum oxide, said surface of said beam irradiation sample irradiated with said laser beam being polished.

* * * * *